(12) United States Patent
Cole

(10) Patent No.: US 7,554,452 B2
(45) Date of Patent: Jun. 30, 2009

(54) INGESTIBLE TRACKING AND LOCATING DEVICE

(76) Inventor: Cary Cole, 2640 Miller Ave., Mt. View, CA (US) 94040

( * ) Notice: Subject to any disclaimer, the term of this patent is extended or adjusted under 35 U.S.C. 154(b) by 481 days.

(21) Appl. No.: 10/894,855

(22) Filed: Jul. 19, 2004

(65) Prior Publication Data
US 2005/0228268 A1 Oct. 13, 2005

Related U.S. Application Data

(60) Provisional application No. 60/488,556, filed on Jul. 18, 2003.

(51) Int. Cl.
G08B 23/00 (2006.01)
A61B 5/05 (2006.01)

(52) U.S. Cl. .................... 340/573.1; 600/424

(58) Field of Classification Search ........... 600/424; 342/357.07, 465; 340/573.1
See application file for complete search history.

(56) References Cited

U.S. PATENT DOCUMENTS

| | | | |
|---|---|---|---|
| 3,719,183 A * | 3/1973 | Schwartz | ............. 600/302 |
| 4,706,689 A | 11/1987 | Man | |
| 4,767,627 A | 8/1988 | Caldwell et al. | |
| 5,246,014 A | 9/1993 | Williams et al. | |
| 5,443,843 A | 8/1995 | Curatolo et al. | |
| 5,629,678 A | 5/1997 | Gargano et al. | |
| 5,629,687 A | 5/1997 | Sutton et al. | |
| 6,120,803 A * | 9/2000 | Wong et al. | ............. 424/473 |
| 6,239,705 B1 * | 5/2001 | Glen | ............. 340/573.1 |
| 6,245,057 B1 | 6/2001 | Sieben et al. | |
| 6,261,601 B1 | 7/2001 | Talwar et al. | |
| 6,559,620 B2 | 5/2003 | Zhou et al. | |
| 6,635,279 B2 | 10/2003 | Kolter et al. | |
| 6,635,281 B2 | 10/2003 | Wong et al. | |
| 6,685,962 B2 | 2/2004 | Friedman et al. | |
| 2002/0010390 A1 * | 1/2002 | Guice et al. | ............. 600/300 |
| 2002/0198470 A1 * | 12/2002 | Imran et al. | ............. 600/587 |
| 2004/0192582 A1 * | 9/2004 | Burnett et al. | ............. 514/2 |

* cited by examiner

*Primary Examiner*—Eric F Winakur
*Assistant Examiner*—Michael T Rozanski
(74) *Attorney, Agent, or Firm*—Levine Bagade Han LLP

(57) ABSTRACT

The present invention relates generally to an electronic tracking and locating system. More specifically, it discloses an electronic tracking and locating system, having a biocompatible housing such that it may be located within the body, either temporarily or for a longer duration.

21 Claims, 3 Drawing Sheets

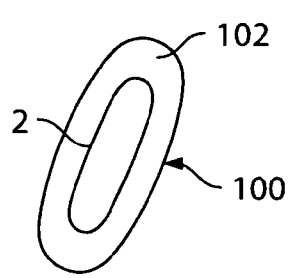 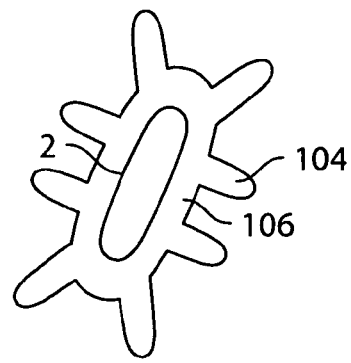
FIG. 2A          FIG. 2B
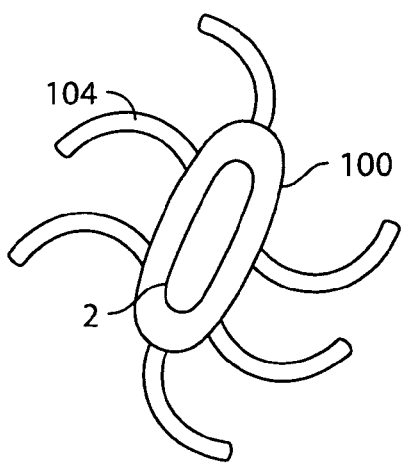 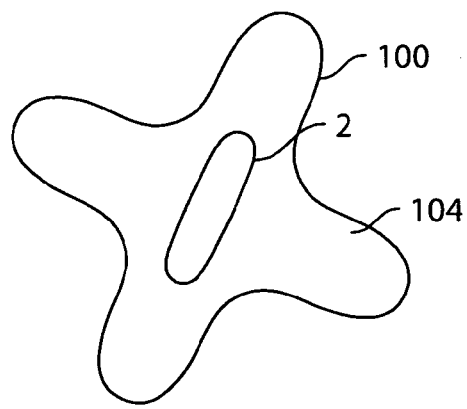
FIG. 2C          FIG. 2D
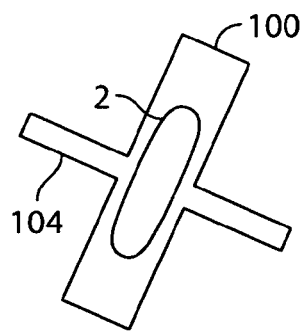
FIG. 2E

INGESTIBLE TRACKING AND LOCATING DEVICE

CROSS REFERENCE TO RELATED APPLICATIONS

This application is a non-provisional of provisional application No. 60/488,556 filed Jul. 18, 2003, the entirety of which is incorporated by reference here.

BACKGROUND OF THE INVENTION

Numerous electronic devices have been introduced to track and locate mobile assets, such as for example, trucks, rail cars, and shipping containers. Hundreds of thousands of these assets have been equipped with tracking and locating devices. The most sophisticated systems permit location of an asset to within a few feet.

More recently, systems to track and locate people have been developed. These tracking and locating devices are useful in managing persons who may be incapable or unable to seek assistance, such as for example, people with Alzheimer's disease, young children, prisoners, and military personnel. Additional systems have been used to track pets and other animals.

Transmitters and transceivers utilized in locating and tracking humans have been worn as bracelets, sewn into clothing, placed in backpacks, implanted behind the ears (U.S. Pat. No. 4,706,689), implanted subdermally (U.S. Pat. No. 5,629,678), or affixed to teeth or gums (U.S. Pat. No. 6,239,705). The entirety of each of these patents are incorporated by reference.

One such system utilizes global positioning satellite technology to track and locate inanimate objects, animals, and humans. In one form, a bracelet containing a receiver is worn by a child. Utilizing the known location of three orbiting satellites and the time it takes for a signal to travel between the transducer and each of the three satellites, a three-dimensional position of the transducer is able to be calculated.

In addition to a receiver being worn as a bracelet, systems have been used employing a self-powered, self-maintained transceiver, surgically implanted under the skin, for locating, tracking and recovering persons in distress such as for example, kidnap victims, people encountering adverse circumstances while in the wilderness, victims of heart attacks, and the like.

Other systems have been used which remain passive until remotely activated. For example, one recovery system employs a transceiver hidden within a motor vehicle and a network of fixed and mobile ground transmitters and receivers to facilitate tracking and recovery of stolen vehicles. The unit is continuously operated as a receiver until it is remotely activated. Once activated, it transmits a radio beacon facilitating tracking and recovery. Ground based fixed and mobile receiver units utilizing field strength measurements and directional receivers then are able to locate the transmitter.

Another system can be affixed to the external surface of a tooth through the use of dental adhesives or bonding agents, or it may be incorporated completely within a dental restoration, endodontically prepared root canal system, a prosthetic tooth or denture.

Location and recovery systems have also been developed using timing and triangulation methods, such as that used by the Emergency Position Indicating Radio Beacons (EPIRB). Using the global positioning satellite system, once the user activates a transmitter, the associated satellite network is capable of locating a transmitting EPIRB anywhere on the face of the globe.

Receivers and transceivers worn as jewelry, sewn into clothing, or placed in the mouth are visible and easily removable, limiting their usefulness for military, intelligence and personal protection applications. Receivers and transceivers implanted under the skin require an invasive surgical procedure to implant these devices, and additional invasive surgical procedures to repair or remove the device. For this reason, sub-dermal implanted devices have a low acceptance rate among potential users, particularly children. Receivers and transceivers implanted in the mouth involve uncomfortable dental procedures to implant these devices, and additional uncomfortable dental procedures to repair or remove the device. For this reason, intra-oral implanted devices have a low acceptance rate among potential users, particularly children. Moreover, various groups have expressed concern over the potential abuse of systems that are implanted due to the inability to easily remove the devices.

In view of the above, there remains a need for an electronic tracking device that overcomes the problems discussed above.

BRIEF SUMMARY OF THE INVENTION

The present invention concerns a temporary electronic tracking and locating system. More specifically, one component of the system includes a device for electronic tracking and locating an individual or animal (the individual or animal being referred to as the "subject"), where the device is configured to be retained in the body, preferably in the stomach or digestive tract for a period of time. This time being referred to as the "retention period."

The invention includes component(s) that transmit or provide a signal through which the subject may be located. The device may be passive (e.g., it may only provide the locating signal upon receipt of an external signal) or active (e.g., it may be in constant or periodic communication with the communication network without the need for an external signal.) In some variations of the invention, the inventive system may temporarily automatically record the location or trail of the subject over a particular period. The system user (e.g., a parent of a lost child) could access the system to obtain the most recent location of the subject (child) in case the temporary or ingestible locating component passes out of the system's range when attempting to locate the subject.

In any case, the structure and configuration of the components depend upon the communication network or networks through which the device enables location of the subject and the many variations of the invention that are described herein.

It is contemplated that the invention is not limited to any particular type of electronic network. The portion of the system that relays information to enable location of the subject (this portion being referred to as the "tag") may be made to communicate through part of any type of communications network such as cellular, wireless, radio frequency identification (RFID), telephone, a public network such as the internet, WIFI, or global positioning satellite network (GPS), etc. It is likely that the invention could use a combination of networks to achieve the result of remote identification. Furthermore, though the tag will work with communication networks to enable location of the subject across large distances, the invention may be suited to work with local communication network or networks so that the tag may temporarily identify a subject located in a building, a complex of buildings, amusement park, campground, national/state park, prison, etc.

After the retention period, the device may pass from the body without the need of invasive medical procedures. One variation of the invention includes a device having a housing that is small enough to be swallowed by a young child. A variation of the invention includes a device that incorporates a structure (e.g., a retention means) that causes the device to be retained within the body, such as the stomach and/or digestive tract, or any other passage of the body, for a period of time. Depending upon the intended use of the device, variations of the invention may be robust enough to function within the body, such as the stomach and/or digestive tract for an extended period of time. In another variation of the invention, the electronic tracking and locating system can be broken down into one or more devices, each for placement within the body, and each having a separate function. For example, one swallowable device can be a receiving unit, and another swallowable device can be the transmitting unit The period of time that the device is retained inside the body may be preselected depending upon the particular application. For example, the retention period may be of a relatively short duration for those individuals engaging in recreational activities such as camping, hiking, sailing, etc. The retention period may be selected to be of a longer duration for such applications as tracking of children, tracking of military, etc.

In accordance with an aspect of the present invention, a concealed electronic tracking and locating device is provided that can be inserted into the body, retained, and maintained internally, for example inside the stomach and/or digestive tract. The device may be conducive to being swallowed. The device may be a single component that is swallowed or may have one or more swallow-able components that permit remote locating of a subject.

Alternatively, variations of the invention include devices that are affixed in a non-surgical manner (e.g., an endoscope, rectoscope, etc.) but naturally expelled by the body after the retention period. Therefore, use of the word non-invasive placement includes placement of the device in a non-surgical manner so that the device will be eventually expelled and in a manner that does not require placing the device underneath tissue (though a portion of the device such as an anchor or line, may be placed within tissue.)

BRIEF DESCRIPTION THE DRAWINGS

FIGS. 2A-2E illustrate variations of the tag or ingestible component of the invention.

DETAILED DESCRIPTION

Example of the System

Figure 1:
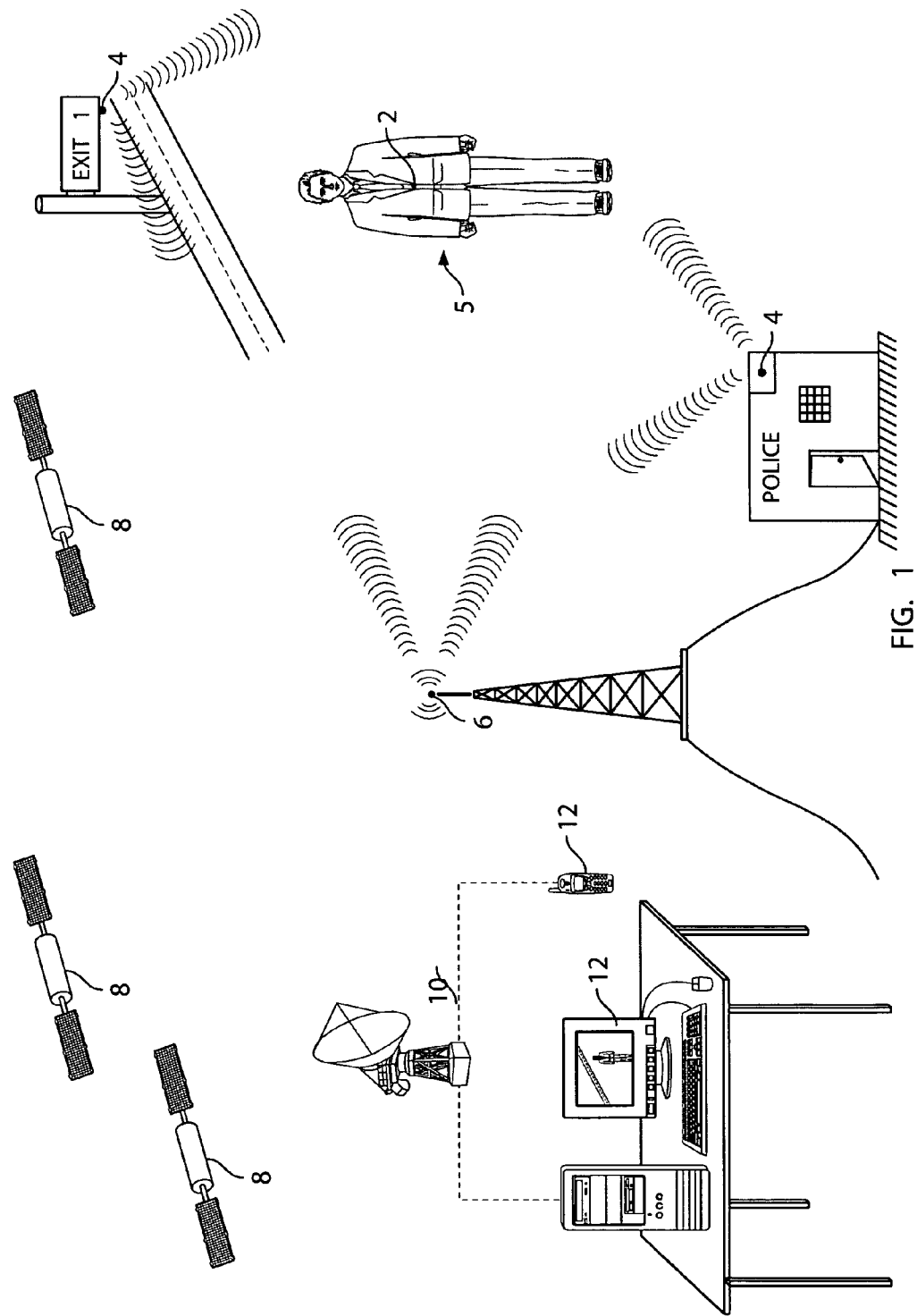
FIG. 1 illustrates the general principle of the invention.

FIG. 1 illustrates the general principle of the invention. It is noted that variations of the invention may include different means for locating the subject. As such, the invention is not limited to those components shown in FIG. 1. Instead, the components of FIG. 1 may vary depending upon the actual type of locating and/or communication system or systems used by tracking and locating system (e.g., GPS, wireless, RFID, telephone, or a public network such as the internet).

As illustrated, the system generally includes a temporary or ingestible tag 2, which is suited for swallowing or non-surgical placement within the body where the tag contains data unique to the subject S. The system also includes a component to determine the location of the tag 2. In the illustrated example, this component is a locator 4 which will generally enable the system to determine the location of a particular tag 2 and communicate with the system so that a person or entity may determine the location of the subject S. In one variation, the locator 4 communicates with a GPS system 8 so that when triggered, it determines the location of the tag 2 (when the tag 2 and locator 4 are combined) or it determines the location of the locator 4 that is communication with the tag 2 (e.g., when the subject S is traveling on a highway and triggers one or more locators 4 along that highway.)

The locator 4 may be placed at a number of locations as a part of a network. For example, a network of locators may be placed within a single building, a complex of buildings, amusement park, campground, national/state park, prison, etc. A number of locators may also be placed at major intersections, along highways, tollbooths, in police cars, in traffic information signs, in AMBER ALERT signs (i.e., signs showing the nationwide/statewide alerts implemented to locate missing or abducted children), hospitals, government/public buildings, etc. The locators 4 may be arranged in any number of sub-networks (e.g., where each state has a sub-network of locators 4 and each county within the state has another sub-network within that state's network. To enable a better locating system, the system may have the ability to search automatically or selectively search each sub-network. Furthermore, the locators 4 may be configured to work with other types of locating systems (e.g., locating systems that are surgically implanted, animal locating systems, etc.)

Alternatively, or in combination with the above, the tag 2 may be physically joined with a locator 4 (such as the case where the tag 2 is a GPS based system.) In such a case, both of these components may be ingestible so that the invention will not rely upon proximity of the tag 2 to a locator 4 for determining the position of the subject.

The system further includes a communications system 6 which transmits data and/or signals regarding the location of a unique tag 2 so that an individual (being remotely located from the subject may determine the location of the subject.) It is contemplated that the communication system 6 may be any type of communication network or combination of networks. The communication network should relay signals between the reader 4 (and tag 2 when the two are combined) and a locating and tracking system processing unit 10. Therefore, the communication system 6 may activate the tag 2 (in those cases where the tag 2 is passive) or may signal the reader 4 to relay information regarding the subject S. The communication system 6 will also transmit data between the reader 4 to the locating and tracking system processing unit 10 where the data may be processed for dissemination to a user interface 12 (e.g., a computer, a cell phone, a unit dedicated to a particular tag 4 etc.). It is also contemplated that the locating and tracking system processing unit 10 may be integrated with a user interface 12.

It is contemplated that there may be many permutations and variations of a tracking and locating system in accordance with the transitory and non-surgical placement of the locating device of the present invention. Therefore, such combinations or other modifications of the present invention are considered to be within the scope of the invention disclosed herein.

Temporary Retension Structure

FIGS. 2A-2E illustrates an example of a tag 2 according to the present invention. The tag 2 will comprise a housing 100 which may be made or coated with a biocompatible material (such as titanium, stainless steel, biocompatible polymer, PTFE, ePFTE, and/or silicone). The housing 100 will contain a suitable material to hold the various components, for example the components being, a board, a wafer, RFID unit, or other substrate material suitable for circuits. The housing 100 will have some mode of allowing for the temporary retention of the tag 2 within the subject's body.

For example, as shown in FIG. 2A, a variation of the inventive tag 2 comprises housing 100 having a composition 102 at least partially surrounding the housing 100 The composition 102 may be in the form of a tablet, capsule, or coating to serve as retaining mechanism for the orally or non-invasive manner. The composition may comprise a gas generating component, a swelling agent (e.g., cross-linked polyvinylpyrrolidone or cross-linked sodium carboxymethylcellulose) a viscolyzing agent (e.g., a carbohydrate gum), and (optionally) a gel forming polymer (e.g., sodium alginate). In some variations the composition may also contain an additional hydrophilic water soluble polymer (e.g., hydroxypropyl methylcellulose). Swelling agents described herein (cross-linked polyvinylpyrrolidone or cross-linked sodium carboxy methylcellulose) may belong to a class of compounds known as super-disintegrants which usually function to promote disintegration of a tablet by absorbing large amounts of water and thereby swelling. This expansion, as well as hydrostatic pressure, cause the tablet to burst. In a tablet which also contains a gas generating component (which may actually be a gas generating couple), one would expect the tablet to disintegrate instantly upon contact with aqueous fluid, if not blow apart. With the use of instantly acting viscolyzing agents, the generated gas is entrapped and the superdisintegrant acts as a swelling agent which swells to, preferably, at least twice its original volume. Thus, the combination of the gas generating component, the swelling agent which is actually a superdisintegrant, and the viscolyzing agent permit the composition to expand such that it is not passed from the body until desired. Examples of such compositions as described above may be found in U.S. Pat. No. 6,261,601 to Talwar et al. the entirety of which is incorporated by reference herein. Coating may also be used to aid in swallowing of the tag 2. Such coatings will be known by having skill in the art.

It should be noted that the composition should be designed such that it does not block food, digestion, etc. Therefore, the composition could be arranged such that only portions of the composition expand. For example, as shown in FIG. 2B, the portions of the composition 102 that expand would allow passage of food or other fluids. With the passage of time, the gel forming polymer produces a cross-linked three-dimensional molecular network resulting in a hydrodynamically balanced system that is retained in the stomach and maintains the tag 2 for a period of time.

In another variation of the invention, the body 100 may include a swellable polymer matrix that swells upon contact with the fluids of the stomach. A portion of the polymer matrix may be surrounded by insoluble material that prevents the covered portion of the polymer matrix from swelling. This configuration prevents expulsion of the tag 2 from the stomach until substantially a desired time passes. For example, when referring to FIG. 2B, the tag 2 may comprise a body 100 having a swellable polymer matrix 104 with areas of insoluble materials 106. It is noted that these variations may be arranged in a number of configurations to provide a shape as desired. In any case, the swellable polymer matrix 104 may form fixed or actuatable extension/expansion members to delay passage of the tag 2 from the body.

Examples of swellable polymers and the composition are described in U.S. Pat. No. 6,120,803 to Wong et al and U.S. Pat. No. 6,635,281 to Wong et al. the entirety of both are incorporated by reference herein. Such polymers include high molecular weight, water-soluble polymers are polyethylene oxide and cellulosic polymer derivatives including hydroxypropyl cellulose, hydroxypropyl methyl cellulose, hydroxyethyl cellulose, sodium carboxy methylcellulose, calcium carboxymethyl cellulose, methyl cellulose, as well as noncellulosics such as maltodextrin, polyvinyl alcohol, polyacrylic acids, alginates, gelatin, natural gums, including guar, lightly crosslinked versions of these polymers, starch graft copolymers and the like. The polymers generally have number average molecular weights over 50,000 grams per mole, such as between 50,000 and 10,000,000 grams per mole and representative viscosities, e.g. for polyethylene oxide in the range of 12-20,000 cps (5% aq, 25.degree. C., MW 100,000-900,000), 400-4000 cps (2% aq, 25.degree. C., MW 1,000,000-2,000,000) and 1500-15,000 cps (1% aq, 25.degree. C., MW 4,000,000-8,000,000) [Brookfield viscometer, rotational spindle]; for methylcellulose in the range of 1,500-18,000 cps (2% aq, 20.degree. C., MW 62,000-134,000) [Ubbelohde tube viscometer]; for hydroxypropyl methylcellulose in the range of 4,000-100,000 cps (2% aq, 20.degree. C., MW 88,000-242,000) [Ubbelohde tube viscometer]; for hydroxyethyl cellulose in the range of 75-400 cps (5% aq, 25.degree. C., MW 90,000-200,000), 400-6500 cps (2% aq, 25.degree. C., MW 300,000-720,000) and 1500-5,000 cps (1% aq, 25.degree. C., MW 1,000,000-1,300,000) [Brookfield viscometer, rotational spindle]; for guar about 5100 cps (1%) [Brookfield viscometer, rotational spindle]; for poly(methyl vinyl ether/maleic anhydride) in the range of 15 to greater than 200 cps (5% aq., MW 20,000-80,000) [Brookfield viscometer, rotational spindle]; for polyvinyl alcohol in the range 27-65 cps (4% aq, 20.degree. C. [Hoeppler falling ball method and 1100-1500 cps (10% aq, 25.degree. C.) [Brookfield viscometer, rotational spindle; for sodium carboxymethyl cellulose in the range of 25-50 cps (2% aq, 25.degree. C.) (MW 90,000) to about 2,500-6,000 cps (1% aq, 25.degree. C.) (MW 700,000) [Brookfield viscometer, rotational spindle]; and for sodium polyacrylic acid 5000-75,000 (0.5% aq) (MW 750,000-4,000,000) [Brookfield viscometer, rotational spindle]. Polymers having molecular weights between 300,000 and 8,000,000 grams per mole are preferred, and those having molecular weights between about 5,000,000 to 8,000,000 grams per mole are especially preferred. Polyethylene oxide having a number average molecular weight between about 5,000,000 to 8,000,000 grams per mole is most especially preferred, e.g. Polyox 308. Also, especially preferred are methylcellulose type/grade A15C, A18M and hydroxypropyl methylcellulose type/grade K4M, K15M, 100M and F4M (Dow Chemical Company); hydroxyethyl cellulose such as Natrosol® HEC; hydroxypropyl cellulose such as Klucel (Grades H, M, G, J, L, E-Aqualon Company); guar such as Supercol® Guar U (Aqualon Company); pectin such as GENU Pectin (Aqualon Company); carrageenan such as GENU Carrageenan (Aqualon Company); poly(methyl vinyl ether/maleic anhydride) such as Gantrez® AN Copolymer (AN-119, -139, -149, -169, -179, GAF Corporation); polyvinyl alcohol such as Elvanol® 71-30, Elvanol® 85-30, Elvanol® 50-42 and Elvanol® HV (DuPont); sodium carboxymethyl cellulose such as Aqualon cellulose gum grade 7H4; sodium polyacrylic acid such as Carpobol® resin grade 934PNF; and polyacrylic acid such as Carpobol® resin grade 934P.

Representative examples of hydroattractants are water-insoluble polymers such as low substituted hydroxypropyl cellulose, microcrystalline cellulose (Avicel), cross-linked sodium or calcium carboxymethyl cellulose, cellulose fiber (Solka-Floc or Elcema), cross-linked polyvinyl pyrrolidone (Polyplasdone XL), cross-linked Amberlite resin, alginates (Satialgine), colloidal magnesium-aluminum silicate (Veegum), corn starch granules, rice starch granules, potato starch granules, wheat starch granules, sodium carboxymethyl starch (Expotab, Primojel), corn starch/acrylamide/sodium acrylate copolymer, acrylamide/sodium acrylate copolymer and the like. A particularly suitable hydroattractant is hydroxypropyl cellulose having a hydroxypropyl content of between about 8-15 weight percent, and preferably about 10-13 weight percent, such as that supplied as Low Substituted Hydroxypropyl Cellulose grade 11 as manufactured by Shin-Etsu Chemical Company, Ltd., Tokyo, Japan.

In another variation of the invention, the tag 2 may comprise a body 100 having a composition 102 where the composition causes the device to float on gastric fluid thereby delaying passage of the tag 2 from the body until the composition 102 is eventually absorbed, or departs from the tag 2. An example of such material includes a blend of polyvinyl acetate and polyvinylpyrrolidone which float on gastric fluids after intake material as described in U.S. Pat. No. 6,635,279 to Kolter et al. the entirety of which is incorporated by reference herein.

It should be noted, that where possible, the compositions described above may be combined to provide a tag 2 that may float in gastric fluids as well as have extension members or protrusion to prevent pre-mature passage from the body. For example, in a variation of the invention, the extension members will be large enough such that the tag 2 become retained in the fundus of the stomach rather than towards the junction of the small intestines or the stomach. In another variation, the extension members may be configured such that they deploy after sufficient time when the tag 2 is located in the small intestines. In either case, the device should be designed such that it does not introduce a health risk by interfering with the passage of food or fluids.

The stomach is the portion of the digestive system most responsible for breaking down food. The lower esophageal sphincter at the top of the stomach regulates food passing from the esophagus into the stomach, and prevents the contents of the stomach from reentering the esophagus. The pyloric sphincter at the bottom of the stomach governs the passage of food out of the stomach into the small intestine.

In another example, the housing 100 can include fixed or actuatable extension/expansion members so the device will not pass from the stomach into the intestinal tract. U.S. Pat. No. 4,767,627 to Caldwell, et al. and U.S. Pat. No. 5,443,843 to Curatolo, et al., each of which is incorporated by reference, describe controlled drug delivery devices that allow devices to be retained in the stomach for extended periods of time. In another embodiment, the housing can be affixed to the stomach wall by coating the device with a material that binds to the stomach wall. In another embodiment, the housing can include fixed or actuatable extension members that attach to the stomach wall. Attachment members/extension members can include hooks, curved needles, or helical or screw tips. The latter are described in U.S. Pat. No. 5,246,014 by Williams et al, which is incorporated herein by reference in its entirety.

The actuatable fixation or extension/expansion members may be actuated via a remote signal, or may be pre-programmed to actuate at a specific time (e.g., 30 seconds after becoming wetted with saliva) and/or upon encountering a specific environment (e.g., stomach acid or change in temperature), or upon encountering a combination of these or other factors or signals. The entire Device or only a portion thereof (i.e., attachment members) can be made from polymers (such as polyethylene glycol, polyethylene oxide or gelatin) that lose strength via erosion or dissolution, hydrolysis or enzymatic degradation so that the Device can be excreted at pre-determined time points (for example, 1 day, 1 month or 1 year). Part of the device also can be made from polymers that lose strength during hydration (such as a cross-linked hydrogel). As used herein, the term "weakening" as applied to material shall include losing strength via erosion, dissolution, hydrolysis, degradation, enzymatic degradation, bioabsorbtion and/or hydration, or any similar mechanism. It is contemplated that the tag 2 may also pass through the body in a normal fashion such that the duration of retention is equal to the normal digestive time of the subject.

FIGS. 2C-2E illustrates another variation of a tag 2 of the present invention having a body or housing 102 with a number of extensions 104 that deploy a short time after the device is swallowed. The extensions 104 may be configured to expand when exposed to fluids for an extended period or gastric fluids when in the stomach such that they do not get caught in the esophagus. Alternatively, or in combination, the tag 2 and housing 100 may be folded and placed within a capsule that dissolves at the appropriate time (e.g., in the stomach or intestines) such that the extension members may deploy and delay passing of the tag 2 from the subject.

TAG Examples

As noted above, the structure of the tag 2 will vary depending upon associated communication network and the mode used to determine location of the subject. For example, if the tag 2 is part of an RFID communication system, the antennas of the system will be found in a number of locations external to the tag 2. In the illustrations above, the antenna of an RFID system is incorporated into the locator 4. The antenna emits radio signals to activate the tag and read data stored within the tag. A number of antennas may be located at any number of different sites. In such a configuration, RFID antennas may be placed at malls, intersections, along highways, tollbooths, in police cars, AMBER ALERT signs, etc. The antenna will activate the tag 2 (in the case of the RFID system, the tag functions as a transponder) when the subject with the tag passes within the range of the antenna. Therefore, in this variation, the tag 2 does not require an integrated power source. Instead, the antenna functions as the tag's the power source. However, the RFID tag 2 may also be combined with a power supply to provide a greater range or to operate with an programmable memory.

The RFID antenna's may be combined with a transceiver and decoder in which case the subsystem functions as a locator 4. Therefore, when the tag 2 passes within the activation zone (or electromagnetic field) of the locator, the activation zone induces a current in the tag. Essentially, the tag automatically detects the locator's activation signal. Then, the induced current in the tag permits the tag to generate a signal unique to that particular tag. The locator receives this unique signal and either decodes the signal or passes it to either a host computer system through a number of communications networks or to the person/entity attempting to locate the subject. The locator may rely upon any type of communications network to relay the information since the locator is not subject to those size limitations that permits swallowing or other such placement of the tag within the body. It is noted that this variation of the invention lends itself to integration with existing locating systems (e.g., hospital tracking devices, Alzheimer patient tracking devices, AMBER ALERT stations, etc.)

Along with the antenna a locator 4 for use with an RFID based system may also include a number of additional components. For example, the locator 4 may also include a GPS component. In such a case, it would not be necessary to pre-map the site of a locator 4, instead, the locator's 4 position can be determined when necessary. Furthermore, including a GPS component allows the locator to be mobile. The locator 4 may also include a communications component (e.g., wireless telephone technology, wireless network capability, or a land-line telephone connection) so that it may send and receive data to and from the tag 2. Furthermore, the locator 4 may also include a memory and/or processing system (e.g., the ability to carry out instructions based on input from an end-user.) In such a case, the locator 4 may record information regarding tags 2 that pass within its range. Or, the locator 4 may receive instructions to only report on a tag 2 or tags 2 having unique characteristics so that, for example, information on every tag 2 that passes within the locator's 4 range is not passed to the processing unit 10.

In another variation of the invention, the tag 2 may be part of a global positioning satellite (GPS) system. In such a case, the tag may comprise a housing which contains a (1) receiver to receive at least one external signal, (2) a passive mode to active mode activator, (3) a signal decoder for determining positional location, (4) a transmitter for transmitting an electromagnetic (EM) signal, (5) an antenna, and (6) a power supply and/or a power storage source. Optionally, an amplifier may be utilized to boost signal strength. In one variation of the invention, the GPS tag 2 will remain passive until activated by the external signal. Upon activation, the GPS tag 2 communicate with GPS positioning satellites to determine the location of the subject. The GPS tag 2 will then transmit a signal via an antenna to an appropriate communications network to convey the location of the subject to a computer system or to the person/entity trying to locate the subject.

GPS components sized for integration with the present invention include but are not limited to: A-GPS Chip Set™, GL-16000GPS Baseband processor provided by Global Locate (Fujitsu), San Jose, Calif. USA; GPS antenna elements E-911 from Spectrum Control Inc., Columbia, Md., USA; D-15 GPS antenna Module from San Jose Navigation Inc., Taipei, Taiwan, ROC; GeoHelix-SMP or GeoHelix-SMP GPS Antenna provided by Sarantel Ltd. Wellingborough, UK. It is understood that the GPS components used in the invention should be compact in size such that the tag may be swallowed by the subject.

Activation

When it is desirable for a person's location to be determined, a signal is transmitted to the device's receiver, for example through a satellite transmitter, cell phone system, RFID network, wireless network, etc. Upon receiving this signal, the device's passive to active mode activator switches the device from the passive mode to active mode, or from an "off to an "on" position. For example, in an RFID system, the signal may simply be the activation field around the locator 4 which allows the tag 2 to generate a signal that is returned to the locator 4. In a GPS system, the tag 2 and locator 4 are one device and a coded signal may turn the device into an active mode.

In another variation, the locator 4 continually determines the information and location of any tag 2 passing within the locator's range, but unless there is a signal from an end-user, the tag's 2 information is not passed from the locator to the communication system. As a safety measure, the locator 4 could store data on a storage unit, for example, for a longer period than the tag 2 is retained in the body. With this configuration, if the subject S is lost and the tag 2 passes before search efforts begin, the system could use the storage function to determine the last recorded location of the subject S.

Once in active mode, a signal decoder for determining positional fix utilizing for example, global positioning satellite technology determines the location of the device. As noted above, in an RFID system, the decoder is usually attached to the locator 4 so that location of the tag 2 can be determined based on the closes locator 4. In a GPS unit, the decoder may be joined to the tag 2. This information is then transmitted via the system's transmitter and antenna to a remotely located locating and tracking processing unit 10. An end-user is then able to determine the location of the tag 2 and hence, the subject S.

Power Source

As discussed above, some variations of the invention require that the tag 2 also include a power source (e.g., an active RFID tag system, a GPS tag system, a cellular tag system, etc.)

In one variation of the invention, the power source is a battery. In another variation, power a self-recharging battery provides power. U.S. Pat. No. 6,559,620 by Zhou et al, which is incorporated by reference herein in entirety, describes various battery self-recharging techniques including placing a transducer in a region of the human body with a substantial temperature gradient wherein the transducer is adapted to generate a potential difference across the recharging cell of the self recharging battery in response to heat flow through the transducer. In another embodiment, the power supply is replaced by a power storage device where the device uses the galvanic ability of the human body to power the device. U.S. Pat. No. 6,245,057 issued to Sieben et al describes a device for treating cancer that can have electrodes on the outside of the device for galvanic current generation upon contact with body fluid. The entirety of U.S. Pat. No. 6,245,057 is hereby incorporated by reference. In yet another variation of the invention, power may be supplied via capacitive coupling and/or placing an electromagnetic induction source close to the body on a regular basis to recharge the energy reservoir. Additional power sources are described in U.S. Pat. Nos. 5,629,687 and 5,629,678 to Gargano et al., the entirety of both of which are incorporated by reference herein.

The present invention may also use firmware or software to control features of the device. For example, the firmware/software may to decode incoming signals, code outgoing signals, trigger the change between active and passive modes, and manage other device operations, or may manage device operations.

Figure 3:
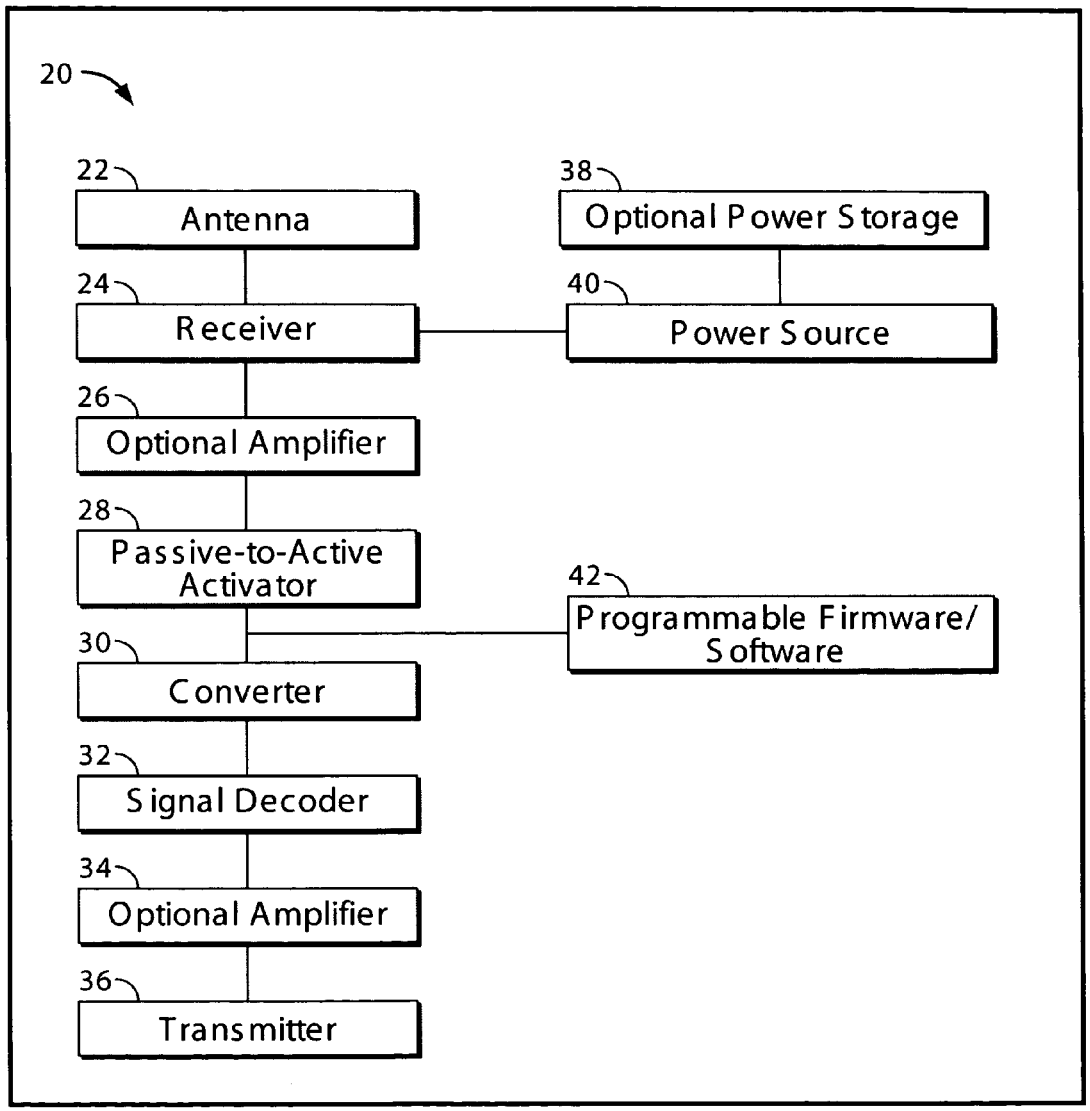
FIG. 3 illustrates a block diagram of a variation of a device of the present invention.

FIG. 3 illustrate a diagram of an example of a device for use with the present invention. The housing (not shown) contains a suitable material to hold the various components, for example, a board, a wafer, or other substrate material 20 suitable for circuits. The integrated circuit optionally, but preferably includes one or more converters 30 for coding internal or external signals. Preferably, the converters 30 are digital converters for coding internal and external digital signals. The integrated circuit further includes a receiver 24 calibrated to receive at least one external signal, passive mode to active mode activator 30, signal decoder 32 for determining positional fix, transmitter 36 for transmitting an electromagnetic signal, antenna 22, programmable software or firmware 42, and power supply 40 for use with the invention. The components are commercially available and/or can be fabricated. Optionally, shielding (not shown) may be provided to protect sensitive anatomical areas from transmission energy and/or one or more amplifiers 86 may be utilized to boost signal strength.

The above illustrations are merely examples of tags for use with the present invention. The invention may be combined with any number modes for determining location. For example, a variation of the invention includes a tag that relies upon wireless telephone systems to locate the user.

The above illustrations are examples of the invention described herein. It is contemplated that combinations of aspects of specific embodiments or combinations of the specific embodiments themselves are within the scope of this disclosure.

What is claimed is:

1. A method for locating a human or animal comprising the steps of: providing an activating signal from a transmitter to activate an electronic component located within the digestive tract of the human or animal, where the electronic component is configured with a swellable polymer matrix that swells upon contact with fluids to form expansion members that prevents passage of the electronic component through the digestive tract to temporarily prevent passage of the electronic component through the digestive tract; activating the electronic component with the activating signal to generate a unique signal; receiving the unique signal; transmitting the unique signal through to an end-user remotely located from the human or animal.

2. The method of claim 1, where the electronic component comprises a radio frequency identification unit.

3. The method of claim 1, where the activating signal comprises an electromagnetic field, which generates a current within the electronic component.

4. The method of claim 1, where the electronic component comprises a global positioning satellite receiver, transmitter, and power supply.

5. The method of claim 1, further comprising recording to the unique signal at a location external to the electronic component.

6. The method of claim 5, where recording the unique signal at the location external to the electronic component comprises recording the unique signal at the transmitter.

7. The method of claim 5, where providing the activating signal occurs as a result of an input by the end-user.

8. The method of claim 1, where the electronic component is configured with a composition that temporarily prevents passage of the electronic component through the digestive tract.

9. The method of claim 8, where the composition comprises a composition selected from the group consisting of a gas generating component, a swelling agent, a viscolyzing agent, a hydrophilic water soluble polymer, and a super-disintegrants.

10. The method of claim 1, where the expansion members are fixed.

11. The method of claim 1, where the expansion members are actuable.

12. The method of claim 1, where the electronic component is configured with a composition that temporarily causes the electronic component to float on gastric fluid.

13. A method for locating a human or animal comprising the steps of: placing a bicompatible housing inside the stomach and/or digestive tract comprising a receiver calibrated to receive at least one external coded signal and a transmitter to transmit a coded electromagnetic signal, and a weakening material attached to the biocompatible housing where the weakening material comprises with a swellable polymer matrix that swells upon contact with fluids to form an expansion member that prevents passage of the electronic component through the digestive tract, where the weakening material retains the device within the body until the weakening material weakens, thereby allowing the device to pass from the body.

14. The method of claim 13, further comprising receiving a coded activating signal, the signal initiating a determination of a positional fix; and transmitting the positional fix to a remotely located receiver.

15. The method of claim 14, wherein the coded signals are encrypted.

16. The method of claim 13, further comprising the step of receiving a coded deactivation signal after the remotely located receiver has received the positional fix.

17. The method of claim 13, where placing a housing inside the stomach comprises swallowing the housing.

18. The method of claim 13, where placing a housing inside the stomach comprises surgically placing the housing.

19. The method of claim 13, where placing a housing inside the stomach comprises endoscopically placing the housing.

20. The method of claim 13, further comprising receiving a coded activating signal; transmitting, upon activation, a signal homing beacon to a remotely located receiver; and homing in on the transmitted signal beacon.

21. The method of claim 20, wherein the signal beacon is received by a receiver selected from the group consisting of a cell phone tower and/or a plurality of orbiting satellites.

* * * * *